US010220205B2

(12) United States Patent
Bhadra et al.

(10) Patent No.: US 10,220,205 B2
(45) Date of Patent: Mar. 5, 2019

(54) SYSTEMS AND METHODS THAT PROVIDE ELECTRICAL STIMULATION TO A NERVE TO REDUCE A REFLEX THAT AFFECTS A BODILY FUNCTION

(71) Applicant: Case Western Reserve University, Cleveland, OH (US)

(72) Inventors: Narendra Bhadra, Chesterland, OH (US); Kenneth J. Gustafson, Shaker Heights, OH (US); Jaime L. McCoin, Pittsburgh, PA (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 29 days.

(21) Appl. No.: 15/380,779

(22) Filed: Dec. 15, 2016

(65) Prior Publication Data

US 2017/0095663 A1    Apr. 6, 2017

Related U.S. Application Data

(62) Division of application No. 14/287,769, filed on May 27, 2014.

(60) Provisional application No. 61/827,024, filed on May 24, 2013.

(51) Int. Cl.
*A61N 1/36* (2006.01)

(52) U.S. Cl.
CPC ..... *A61N 1/36007* (2013.01); *A61N 1/36014* (2013.01); *A61N 1/36017* (2013.01); *A61N 1/36057* (2013.01); *A61N 1/36171* (2013.01); *A61N 1/36178* (2013.01)

(58) Field of Classification Search
CPC ............ A61N 1/36007; A61N 1/36017; A61N 1/36171; A61N 1/0551; A61N 1/3606; A61N 1/08; A61N 1/3605; A61N 1/36196; A61N 1/36057; A61N 1/05; A61B 5/04001; A61B 5/205; A61B 5/4836; A61M 2205/054; A61M 5/1723; A61M 2210/1085; A61M 2210/1089; A61M 5/14276; Y10S 128/25
See application file for complete search history.

(56) References Cited

U.S. PATENT DOCUMENTS

| 7,142,985 | B2 | 11/2006 | Edwards |
| 7,623,925 | B2 | 11/2009 | Grill |
| 7,805,203 | B2 | 9/2010 | Ben-David |
| 2009/0254144 | A1 | 10/2009 | Bhadra et al. |
| 2012/0101326 | A1 | 4/2012 | Simon |

OTHER PUBLICATIONS

Boger et al., "Bladder Voiding by Combined High Frequency Electrical Pudendal Nerve Block and Sacral Root Stimulation", Neurourology and Urodynamics, 2008, 27, pp. 435-439.

(Continued)

*Primary Examiner* — Deborah Malamud
(74) *Attorney, Agent, or Firm* — Tarolli, Sundheim, Covell & Tummino LLP

(57) ABSTRACT

One aspect of the present disclosure relates to a system for electrical stimulation. A waveform generator can be configured to generate an electrical waveform. An electrode can be electrically coupled to the waveform generator and configured to deliver the electrical waveform to a nerve to reduce at least one reflex that affects a bodily function.

7 Claims, 13 Drawing Sheets

(56) References Cited

OTHER PUBLICATIONS

Brindley, "An Implant to Empty the Bladder or Close the Urethra", Journal of Neurology, Neurosurgery, and Psychiatry, 1977, 40, pp. 358-369.
Buss et al., "Sacral Dorsal Horn Neurone Activity During Micturition in the Cat", Journal of Physiology, 2003, 551.1, pp. 387-396.
Chang et al., "Serotonergic Drugs and Spinal Cord Transections Indicate that Different Spinal Circuits are Involved in External Urethral Sphincter Activity in Rats", Am J Physiol Renal Physiol, 2007, 292, F1044-F1053.
de Groat et al., "Organization of the Neural Switching Circuitry Underlying Reflex Micturition", Acta Physiol (Oxf), Jan. 2013, 207(1), pp. 66-84.
de Groat, "Plasticity of Bladder Relfex Pathways During Postnatal Development", Physiology & Behaivor, 2002, 77, pp. 689-692.
deGroat et al., "Changes in Somato-Vesical Reflexes During Postnatal Development in the Kitten", Brain Research, 1975, 94, pp. 150-154.
Fowler et al., "The Neural Control of Micturition", Nat Rev Neurosci., Jun. 2008, 9(6), pp. 453-466.
Gaunt et al., "Control of Urinary Bladder Function with Devices: Successes and Failures", Prog Brain Res, 2006, 152, pp. 163-194.
Van Kerrebroeck et al., "Results of Sacral Neuromodulation Therapy for Urinary Voiding Dysfunction: Outcomes o a Prospective, Worldwide Clinical Study", The Journal of Urology, Nov. 2007, vol. 178, pp. 2029-2034.
Kirkham et al., "Neuromodulation Through Sacral Nerve Roots 2 to 4 with a Finetech-Brindley Sacral Posterior and Anterior Root Stimulator", Spinal Cord, 2002, 40, pp. 272-281.
Mahfouz et al., "Management of Detrusor External Sphincter Dyssynergia in Neurogenic Bladder", Eur J Phys Rehabil Med, 2011,47, pp. 639-650.
Mariano et al., "Suppression of Reflex Urethral Responses by Sacral Dermatome Stimulation in an Acute Spinalized Feline Model", Neurourol Urodyn, Mar. 2010, 29(3), pp. 494-500.
Opisso et al., "Patient Controlled Versus Automatic Stimulation of Pudendal Nerve Afferents to Treat Neurogenic Detrusor Overactivity", The Journal of Urology, Oct. 2008, vol. 180, pp. 1403-1408.
Pan et al., "Long-Term Outcomes of External Sphincterotomy in a Spinal Injured Population", The Journal of Urology, Feb. 2009, vol. 181, pp. 705-709.
Shefchyk, "Sacral SpinalInterneurones and the Control of Urinary Bladder and Urethral Striated Sphincter Muscle Function", Journal of Physiology, 2001, 533.1, pp. 57-63.
Tai et al., "Spinal Reflex Control of Mictruition After Spinal Cord Injury", Restor Neural Neurosci., 2006, 24(2), pp. 69-78.
Weld et al., "Clinical Significance of Detrusor Sphincter Dyssynergia Type in Patients with Post-Traumatic Spinal Cord Injury", Urology, 2000, 56(4), pp. 565-568.

SYSTEMS AND METHODS THAT PROVIDE ELECTRICAL STIMULATION TO A NERVE TO REDUCE A REFLEX THAT AFFECTS A BODILY FUNCTION

RELATED APPLICATIONS

This application is a divisional application of U.S. Patent Application Ser. No. 14/287,769, filed May 27, 2014, which claims the benefit of U.S. Provisional Application No. 61/827,024, filed May 24, 2013, entitled "Surface Electrical Stimulation for Sensory Feedback to Improve Bladder Voiding in Neurological Disorders," (now Expired). The entirety of each of the aforementioned applications is hereby incorporated by reference for all purposes.

GOVERNMENT FUNDING

This work was made with government support under Grant No DK077089 and grant number EB004314 from the Department of Health and Human Services, National Institutes of Health. This work was also made with government support under Grant No RR&D668 from the Department of Veterans Affairs. The United States government has certain rights in the invention.

TECHNICAL FIELD

The present disclosure relates generally to neural stimulation and, more specifically, to systems and methods that can provide electrical stimulation to a nerve to reduce a reflex that affects a bodily function.

BACKGROUND

Individuals with neurologic disease or injury can suffer from disordered genitourinary function. For example, in the majority of individuals with spinal cord injuries (SCIS) spinal reflexes (e.g., external urethral sphincter (EUS) reflexes) can become hyper-responsive to sensory input from the bladder and other pelvic nerves, prevent coordinated bladder-sphincter contraction, and inhibit bladder evacuation, leading to urine retention and increased bladder pressure, which can damage the bladder, the kidneys, or other parts of the urinary tract.

Current clinical standards for treating urethral spasms include intermittent catheterization, sphincterotomy, urethral stents, pudendal nerve transection and/or pudendal nerve block. However, each of these clinical standards is limited by factors, including severe spasticity, poor upper limb function or urinary incontinence. Sacral anterior root stimulation combined with dorsal rhizotomy can combat these factors by abolishing the urethral reflexes that inhibit bladder evacuation. However, dorsal rhizotomy is not widely accepted because it can eliminate residual bowel and sexual functions.

SUMMARY

The present disclosure relates generally to neural stimulation and, more specifically, to systems and methods that can provide electrical stimulation to a nerve to reduce a reflex that affects a bodily function. As an example, the electrical stimulation can affect one or more urethral reflexes that cause disordered urinary bladder function in individuals with spinal cord injuries (SCIs) to provide effective bladder evacuation without interfering with existing neural capacities (e.g., residual bowel and sexual functions).

In one aspect, the present disclosure can include a system for electrical stimulation. A waveform generator can be configured to generate an electrical waveform. An electrode can be electrically coupled to the waveform generator and configured to deliver the electrical waveform to a nerve to reduce at least one reflex that affects a bodily function.

In another aspect, the present disclosure can include a method for affecting a bodily function in a subject. The method can include the step of generating, by a waveform generator, an electrical waveform. The method can also include the step of delivering, by an electrode coupled to the waveform generator, the electrical waveform to a nerve that includes an afferent nerve fiber of the subject to stimulate the afferent nerve fiber to affect the bodily function.

In a further aspect, the present disclosure can include a neural prosthesis that can provide urinary bladder control in a subject. The neural prosthesis can include a waveform generator configured to generate an electrical waveform. The electrical waveform can be configured to reduce at least one urethral reflex that can impede urine flow from a urinary bladder of the subject. The neural prosthesis can also include an electrode configured to deliver the electrical waveform to a nerve of the subject. The electrical waveform can cause an afferent nerve fiber within the nerve to generate at least one action potential to reduce the at least one urethral reflex and facilitate voiding of the urinary bladder.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
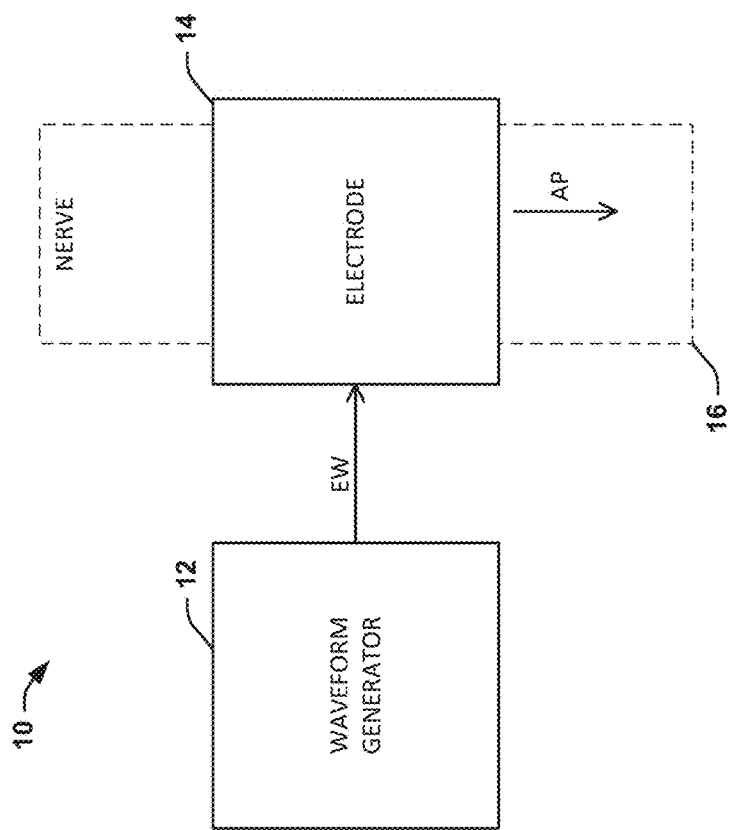
FIG. 1 is a schematic block diagram showing a system for electrical stimulation that can stimulate a reflex of a subject in accordance with an aspect of the present disclosure.

In the context of the present disclosure, the singular forms "a," "an" and "the" can also include the plural forms, unless the context clearly indicates otherwise. The terms "comprises" and/or "comprising," as used herein, can specify the presence of stated features, steps, operations, elements, and/or components, but do not preclude the presence or addition of one or more other features, steps, operations, elements, components, and/or groups. As used herein, the term "and/or" can include any and all combinations of one or more of the associated listed items. Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "reflex" can refer to an involuntary and nearly instantaneous response to a stimulus that involves a nerve impulse passing inward from a receptor to the spinal cord and outward to an effector without reaching the level of consciousness. In some instances, a "spinal reflex" can occur without passing to the brain. An example of a spinal reflex is an afferent-mediated spinal reflex.

As used herein, the term "bodily function" can refer to a process of a subject's body. In some instances, a bodily function can be affected by one or more reflexes. Examples of bodily functions can include urination (bladder voiding), defecation, digestion, and the like. The terms "bodily function" and "biological function" can be used interchangeably herein.

As used herein, the term "neural stimulation" can refer to application of a stimulus waveform to a nerve that can substitute for a neurological function (e.g., motor function, sensory function, cognitive function, etc.) that has been damaged (e.g., as a result of a neurological disorder). In some instances, neural stimulation can be used to relax or suppress a spinal cord reflex that affects a bodily function. For example, neural stimulation of a nerve can cause a muscle associated with a reflex motion to relax and allow the bodily function to occur. The terms "neural stimulation" and "neural modulation" can be used interchangeably herein. A "neural prosthesis" can refer to one or more devices that can accomplish neural stimulation.

As used herein, the term "stimulus waveform" can refer to a signal that can be applied to a nerve to accomplish neural stimulation. For example, the stimulus waveform can cause one or more nerve fibers to generate an action potential. In some instances, a stimulus waveform can be an electrical waveform, a heat waveform, a light waveform, and/or a radio frequency waveform.

As used herein, the term "electrical waveform" can refer to an electrical signal that can be generated by a waveform generator and applied to a nerve with an electrode to achieve neural stimulation. In some instances, the electrical waveform can be a mathematical description of a change in voltage over time (or "voltage controlled") or a change in current over time (or "current controlled"). In some instances, the electric waveform can be a monophasic waveform with an anodic phase or a cathodic phase. In other instances, the electric waveform can be a biphasic waveform with an anodic phase and a cathodic phase.

As used herein, the term "nerve" can refer to a fiber or bundle of fibers that can transmit signals. One example of a nerve is a "peripheral nerve." Generally, a peripheral nerve can refer to a nerve in a subject's body other than brain and spinal cord. A peripheral nerve can include a bundle of fibers (including motor and/or autonomic ("efferent") and sensory ("afferent") fibers) that can connect the brain and spinal cord to the rest of the patient's body. In some instances, the peripheral nerve can conduct information bi-directionally (e.g., providing both motor control and sensory feedback). Other examples of nerves can include a bladder efferent nerve, an afferent-mediated peripheral nerve, a sacral spinal cord nerve, a sacral root nerve, and a lumber spinal cord nerve As used herein, the term "afferent nerve" can refer to one or more nerve fibers that can carry a signal from a sensory receptor to the spinal cord. One example of an afferent nerve is a sensory nerve.

As used herein, the term "efferent nerve" can refer to one or more nerve fibers that can carry a signal from the spinal cord to a muscle receptor and/or organ.

As used herein, the term "signal" can refer to one or more action potentials generated within one or more nerve fibers and conducted through the one or more nerve fibers to a synapse to facilitate the release of one or more neurotransmitters.

As used herein, the term "subject" can refer to any warm-blooded organism including, but not limited to, a human being, a pig, a rat, a mouse, a dog, a cat, a goat, a sheep, a horse, a monkey, an ape, a rabbit, a cow, etc. The terms "subject" and "patient" can be used interchangeably herein.

II. Overview

The present disclosure relates generally to neural stimulation and, more specifically, to systems and methods that can provide electrical stimulation to a nerve to reduce a reflex that affects a bodily function. The systems and methods described herein can provide electrical stimulation to one or more nerves to reduce a reflex that affects a bodily function. An electrical waveform configured to reduce the reflex can be generated and delivered to one or more nerves. One or more fibers within the nerve can be activated to reduce at least one reflex that affects a bodily function. Accordingly, the bodily function can proceed uninhibited by the reflex.

In some instances, the bodily function can be bladder and/or urethra control. Trauma to the central nervous system (e.g., due to a spinal cord injury (SCI) or a neurological disorder) can lead to a disruption in voluntary control over the muscles and organs below the level of injury. Subjects that have experienced such trauma can experience loss of bladder control and the emergence of dyssynergic reflex patterns. Reflex contractions of the external urethral sphincter (EUS) can become uncoordinated from bladder contractions, which can result in high bladder pressures, uterovesical reflux, and poor bladder emptying, which can lead to serious medical complications. The systems and methods described herein can apply neural stimulation to one or more spinal circuits (e.g., sacral circuits and/or lumbar circuits) to reduce bladder and sphincter (e.g., external urethral sphincter (EUS)) reflexes and improve bladder control in subjects that have experienced trauma to the central nervous system without requiring a dorsal rhizotomy.

III. Systems

One aspect of the present disclosure can include a system that can apply electrical stimulation to stimulate a reflex of a subject. In some instances, the system can provide electrical stimulation via an electrical waveform to one or more nerves (that include one or more afferent nerve fibers) to reduce a reflex that affects a bodily function. For example, the electrical waveform can be a patterned waveform. The patterned waveform can include a base frequency. Each cycle of the base frequency can include a stimulus waveform. For example, the stimulus waveform can occupy at least 50% of each cycle of the base frequency. In another example, the stimulus waveform can be a burst waveform (generally of the form described by Bhadra et al. in U.S. patent application Ser. No. 12/417,529, the contents of which are hereby incorporated by reference herein). In a further example, electrical waveform can be a burst waveform (generally of the form described by Bhadra et al. in U.S. patent application Ser. No. 12/417,529).

As shown in FIG. 1, one aspect of the present disclosure can include a system 10 configured to apply electrical stimulation to stimulate a reflex of a subject. In some instances, the electrical stimulation can activate one or more sensory fibers within the nerve. The activation of the one or more sensory fibers can reduce one or more reflexes that can impede a bodily function. For example, the bodily function can be voiding the bladder, and the reflexes can include one or more urethral reflexes. Although system 10 is described with respect to urethral reflexes and urinary voiding, it will be understood that the electrical stimulation of system 10 can be used in connection with any bodily function that can be impeded or facilitated by one or more reflexes (e.g., bowel evacuation, digestion, etc.).

The system 10 can include components including at least a waveform generator 12 and an electrode 14. In some instances, the waveform generator 12 can include a non-transitory memory and/or a processor. The non-transitory memory can store instructions, and the processor can facilitate execution of the instructions to generate an electrical waveform.

The waveform generator 12 can be configured to generate an electrical waveform (EW). The electrical waveform (EW) can be configured to facilitate reduction of at least one reflex that affects a bodily function. For example, the electrical waveform (EW) can be a patterned waveform.

Figure 6:
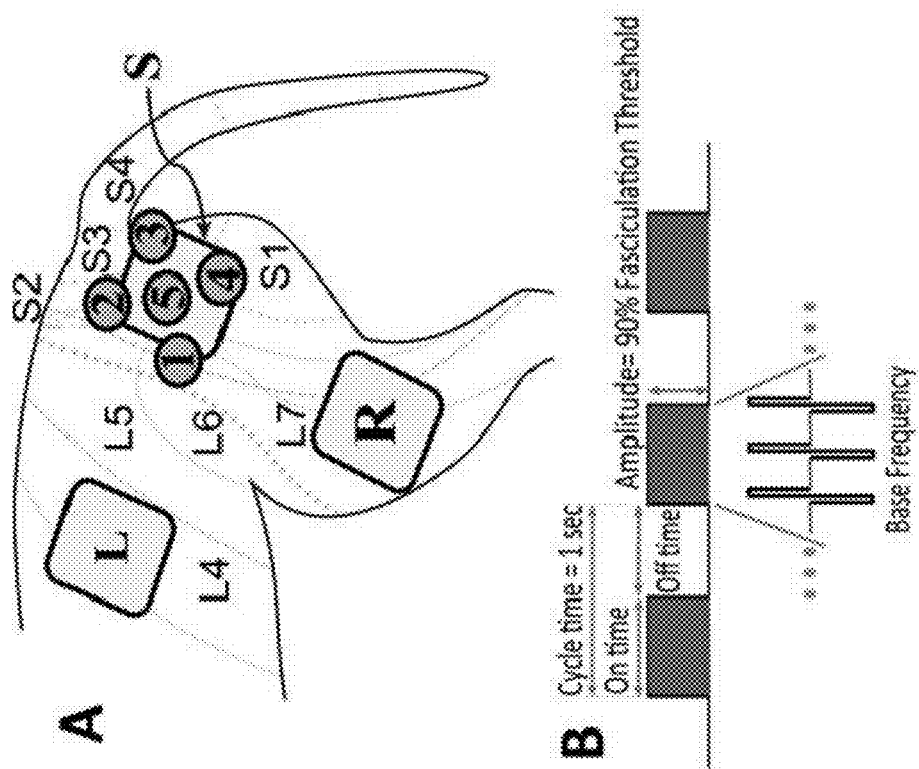
FIG. 6 is an example of surface electrode placement and patterned stimulus waveforms used to reduce aberrant urethral reflexes of a feline.

The patterned waveform can include a base frequency (an example of a patterned waveform in shown in FIG. 6). In some instances, the base frequency can be 10 Hz or less. In other instances, the base frequency can be 5 Hz or less. In still other instances, the base frequency can be 1 Hz or less.

A stimulation waveform can be delivered during each duration of the base frequency. In some instances, the stimulation waveform can be delivered during 50% or more of each duration of the base frequency. In other instances, the stimulation waveform can be delivered during 60% or more of each duration of the base frequency. In still other instances, the stimulation waveform can be delivered during 75% or more of the base frequency. In another instance, the stimulation waveform can be delivered during 100% of the base frequency.

The stimulation waveform can be of a greater frequency than the base frequency. In some instances, the stimulation waveform can have a frequency of more than 5 Hz. In other instances, the stimulation waveform can have a frequency of 15 Hz or more. In still other instances, the stimulation waveform can have a frequency of 20 Hz or more.

The electrode 14 can be electrically coupled to the waveform generator to receive the electrical waveform (EW) from the waveform generator 12. The electrode 14 can include one or more contacts to facilitate delivery of the electrical waveform (EW) to facilitate activation of the nerve 16. In some instances the electrode 14 can be a surface electrode that can deliver the electrical waveform (EW) to a nerve that is located in proximity to the skin (e.g., a dermatome). In other instances, the electrode 14 can be a subcutaneous electrode that can deliver the electrical waveform (EW) to a nerve that is located either in proximity to the skin or at a distance below the skin.

The electrode 14 can be configured to deliver the electrical waveform (EW) to stimulate a nerve 16 to reduce at least one reflex that affects a bodily function. For example, the electrical waveform (EW) can stimulate the nerve 16 to produce a signal, including one or more action potentials (AP) that can ultimately reduce the one or more reflexes. In some instances, the electrical waveform (EW) can be configured to stimulate at least an afferent nerve fiber of the nerve 16 to generate a signal that can include an action potential (AP) and transmit the signal to the spinal cord. The spinal cord can reflexively send a signal that can include an action potential through at least one efferent nerve fiber to affect one or more muscles associated with the reflex. An action of the muscles that can be induced by the signal from the efferent nerve fiber can affect a bodily function.

Figure 2:
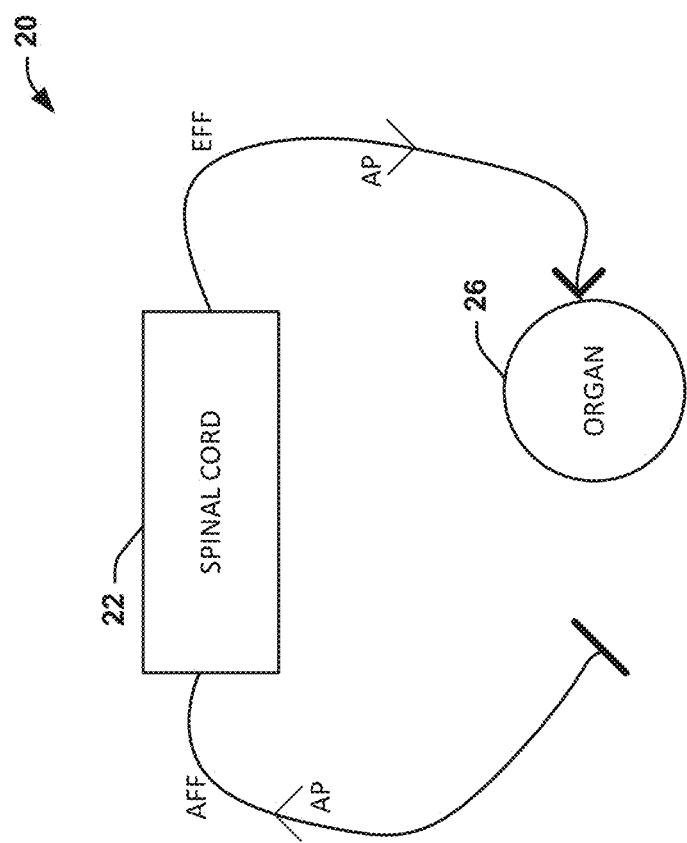
FIG. 2 is a schematic diagram showing an example of a spinal reflex that can be stimulated by the system shown in FIG. 1.

An example of an afferent-mediated reflex pathway 20 is shown in FIG. 2. The reflex pathway 20 can include an afferent nerve fiber (AFF) and an efferent nerve fiber (EFF). Although the afferent nerve fiber (AFF) and the efferent nerve fiber (EFF) are illustrated as separate, in some instances, these fibers can be included in the same nerve. Additionally, although the afferent nerve fiber (AFF) and the efferent nerve fiber (EFF) are illustrated as single fibers, in some instances, the afferent nerve fiber and/or the efferent nerve fiber can include one or more nerve fibers.

The afferent nerve fiber (AFF) can receive a sensory input and transmit a signal (AP) to a portion of the spinal cord 22 (e.g., the sacral portion of the spinal cord or the lumbar portion of the spinal cord). For example, the sensory input can be received by a dermatome linked to a certain portion of the spinal cord.

In response, the spinal cord 22 can transmit a signal (AP) along one or more efferent nerve fibers (EFF). The signal (AP) can be transmitted by the efferent nerve fibers to activate or disable a reflex action that can affect an organ 26. In some instances, the efferent nerve fibers (EFF) can be autonomic nerve fibers (e.g., sympathetic nerve fibers and/or parasympathetic nerve fibers).

One example of a reflex can include a urethral reflex (e.g., an external urethral sphincter reflex or an internal urethral sphincter reflex). The urethral reflex can impede one or more bodily functions (e.g., voiding the urinary bladder). For example, the system 10 of FIG. 1 can selectively void the urinary bladder when the urethral reflex is reduced.

The system 10 can provide a non-destructive, minimally-invasive treatment for spastic urethral reflex contractions. The urethral reflex can be reduced by stimulating a nerve that includes one or more afferent fibers (e.g., a peripheral nerve, a sacral spinal cord nerve, a sacral root nerve, and/or a lumber spinal cord nerve) with the electrical waveform (EW). In some instances, the electrical waveform (EW) can be a patterned electrical waveform that can include a stimulus during at least a portion of the duty cycle. In some instances, the stimulus waveform can be a burst waveform.

The one or more afferent nerve fibers can relay the send a signal induced by the stimulus waveform to the spinal cord. The spinal cord can signal one or more efferent nerve fibers to relax the spastic urethral reflex. When the spastic urethral reflex is relaxed, the urinary bladder can be voided.

In some instances, the voiding of the urinary bladder can be activated by a bladder driver. For example, the bladder driver can apply an electrical stimulation to at least one of a sacral root, a bladder efferent nerve, and an afferent-mediated peripheral nerve to activate the urinary bladder for voiding. The bladder driver can also be a bladder reflex elicited by an individual such as bladder tapping or bladder pressure generated by crede or valsalva maneuvers.

IV. Methods

Another aspect of the present disclosure can include methods that can utilize electrical stimulation to stimulate a reflex of a subject. In some instances, the methods can provide electrical stimulation via an electrical waveform to one or more nerves (that include one or more afferent nerve fibers) to reduce a reflex that affects a bodily function. For example, the electrical waveform can be a patterned waveform. The patterned waveform can include a base frequency. Each period of the base frequency can include a stimulus waveform. For example, the stimulus waveform can occupy at least 50% of each period of the base frequency. In another example, the stimulus waveform can be a burst waveform.

Although the methods are described with respect to urethral reflexes and urinary voiding, it will be understood that the electrical stimulation of system 10 can be used in connection with any bodily function that can be impeded or facilitated by one or more reflexes (e.g., bowel evacuation, digestion, etc.).

Figure 3:
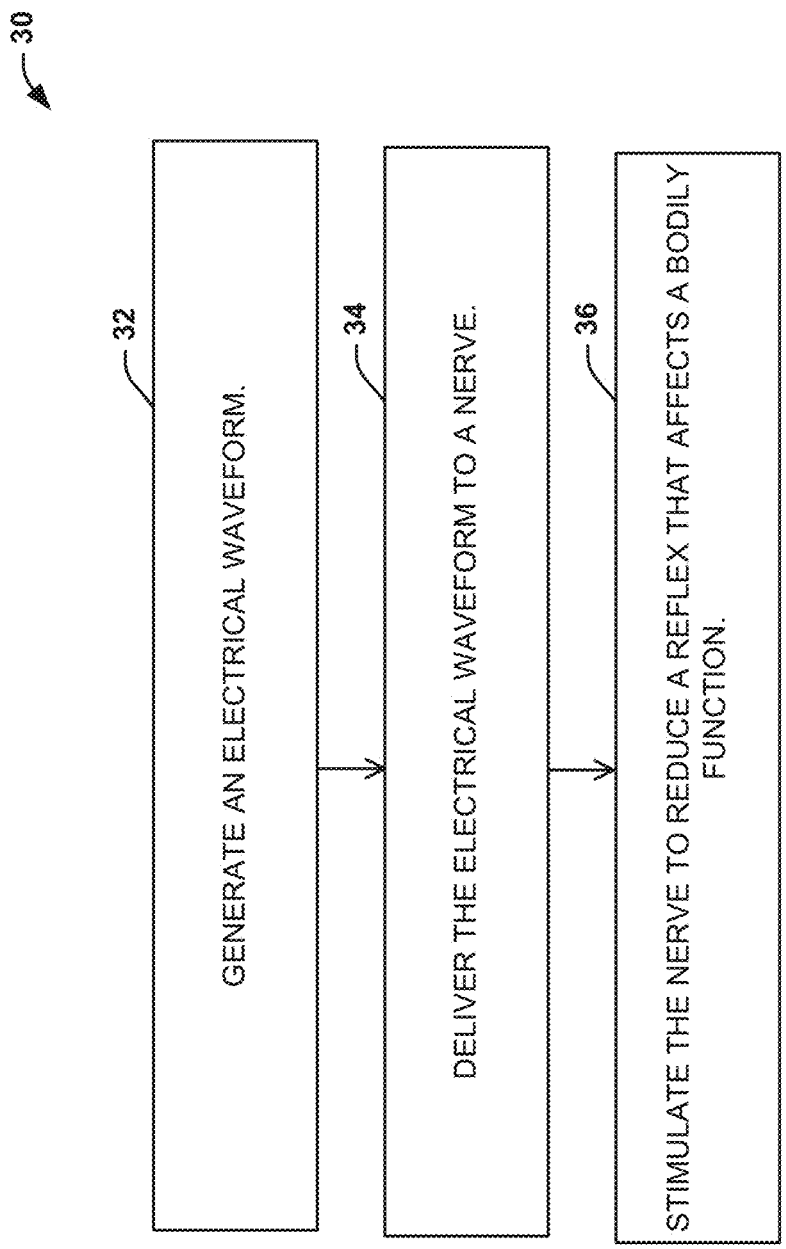
FIG. 3 is a process flow diagram illustrating a method for electrical stimulation that can stimulate a reflex of a subject in accordance with another aspect of the present disclosure.
Figure 4:
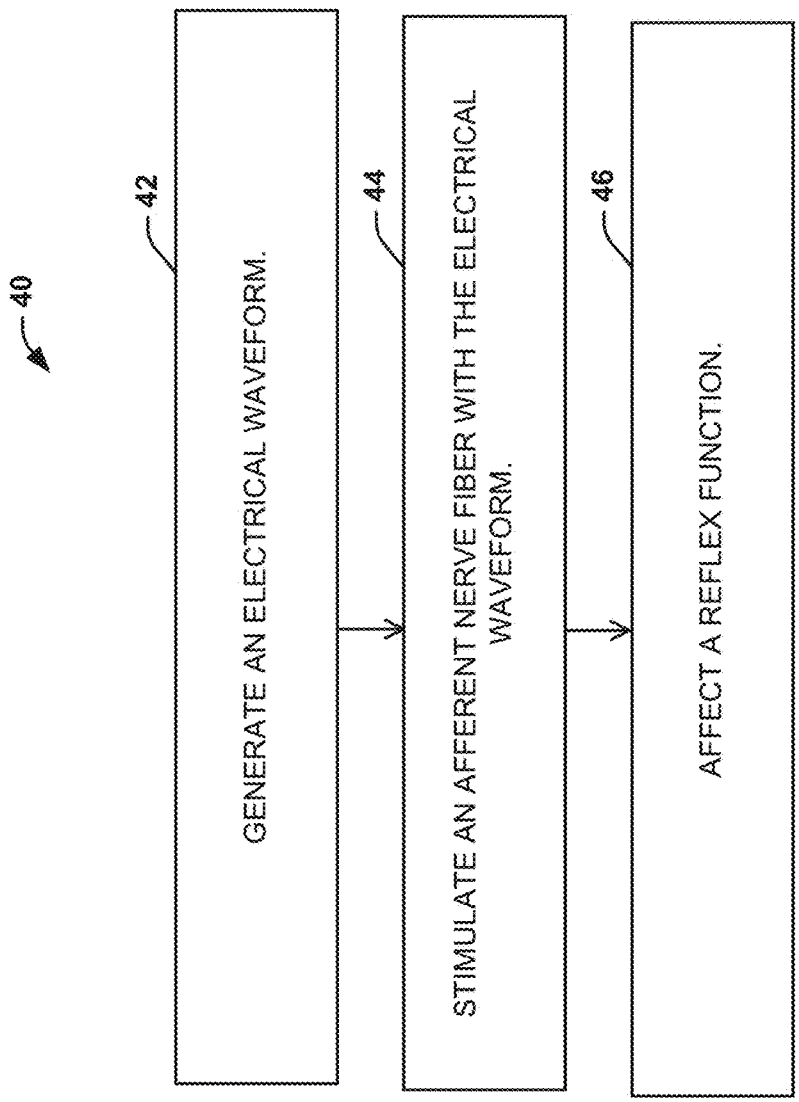
FIG. 4 is a process flow diagram illustrating an example application of the method shown in FIG. 3 for electrical stimulation of an afferent nerve fiber of a nerve to affect the reflex of the subject.

An example of a method 30 that can use electrical stimulation to stimulate a reflex of a subject is shown in FIG. 3. Another example of a method 40 that can use electrical stimulation to activate an afferent nerve fiber to affect the reflex of the subject is shown in FIG. 4. A further example of a method 50 that can use electrical stimulation of the afferent fiber to reduce a urethral reflex to facilitate voiding the urinary bladder of the subject is shown in FIG. 5.

Figure 5:
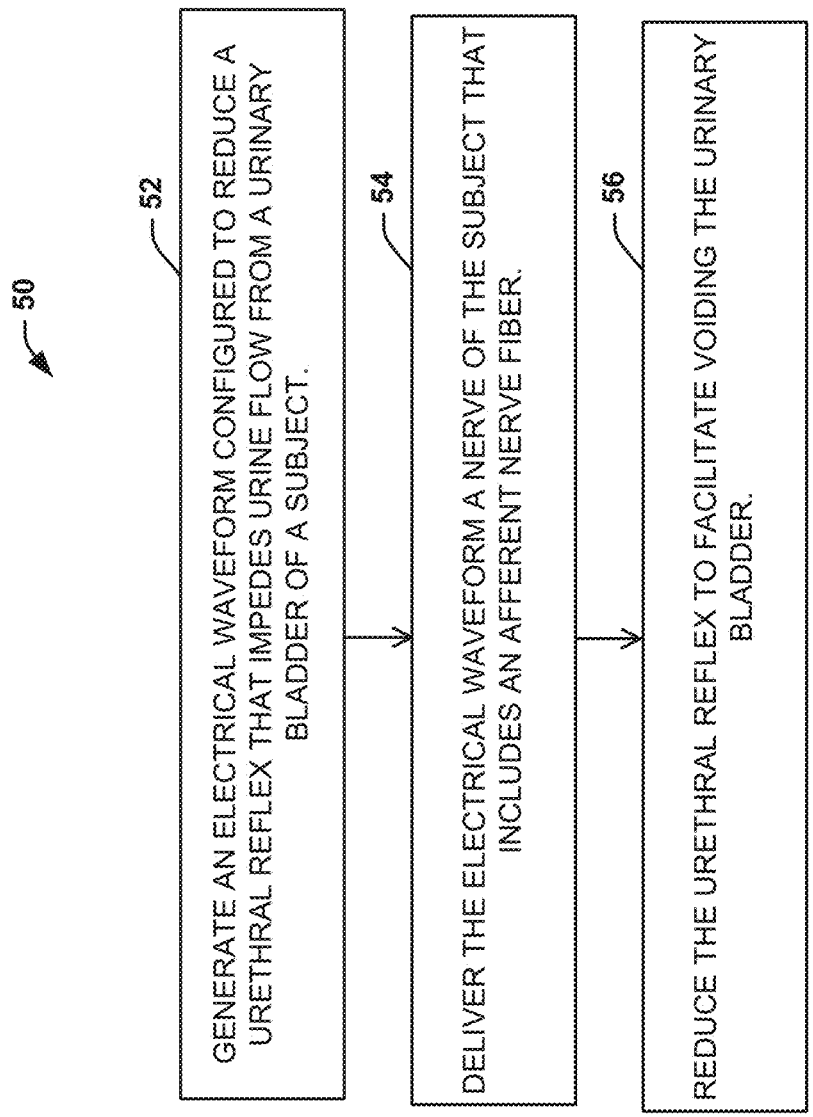
FIG. 5 is a process flow diagram illustrating an example application of the method shown in FIG. 3 for electrical stimulation of the afferent fiber of the nerve to reduce the urethral reflex to facilitate voiding the urinary bladder of the subject.

The methods 30, 40, and 50 of FIGS. 3, 4, and 5, respectively, are illustrated as process flow diagrams with flowchart illustrations. For purposes of simplicity, the methods 30, 40, and 50 are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 30, 40, and 50.

Referring to FIG. 3, an aspect of the present disclosure can include a method 30 for electrical stimulation that can stimulate a reflex of a subject. The reflex can be at least one reflex that can impede a bodily function. For example, the reflex can be a urethral reflex that can impede urinary voiding.

At 32, an electrical waveform (e.g., EW) can be generated (e.g., by a waveform generator 12). The electrical waveform can be configured to facilitate reduction of the at least one reflex that affects a bodily function. For example, the electrical waveform can be a patterned waveform. The patterned waveform can include a base frequency. In some instances, the base frequency can be 10 Hz or less. In other instances, the base frequency can be 5 Hz or less. In still other instances, the base frequency can be 1 Hz or less.

A stimulation waveform can be delivered during each duration of the base frequency. In some instances, the stimulation waveform can be delivered during 50% or more of each duration of the base frequency. In other instances, the stimulation waveform can be delivered during 60% or more of each duration of the base frequency. In still other instances, the stimulation waveform can be delivered during 75% or more of the base frequency. In further instances, the stimulation waveform can be delivered during 100% of the base frequency.

The stimulation waveform can be of a greater frequency than the base frequency. In some instances, the stimulation waveform can have a frequency of more than 10 Hz. In other instances, the stimulation waveform can have a frequency of 15 Hz or more. In still other instances, the stimulation waveform can have a frequency of 20 Hz or more.

At 34, the electrical waveform can be delivered to a nerve (e.g., by an electrode 14). In some instances the electrode can deliver the electrical waveform to the nerve via one or more surface contacts and/or subcutaneous contacts. For example, the nerve can be located in proximity to the skin (e.g., a dermatome). In another example, nerve can be located at a distance below the skin.

At 36, the nerve can be stimulated (e.g., by EW) to reduce a reflex that affects a bodily function. In some instances, the stimulation by the electrical waveform can activate one or more sensory fibers within the nerve (e.g., to generate one or more action potentials). The activation of the one or more sensory fibers can ultimately reduce one or more reflexes that can impede (or otherwise affect) the biological function. In some instances, the activated afferent fibers can signal the spinal cord, which can activate one or more efferent fibers to reduce the one or more reflexes. For example, the one or more efferent fibers can reduce one or more spastic urethral reflexes, which can impede voiding the urinary bladder.

FIG. 4 shows an example application of the method 30 shown in FIG. 3. The method 40 of FIG. 4 relates to electrical stimulation of an afferent nerve fiber of a nerve to affect the reflex of the subject. In some instances, the afferent nerve fiber can be a sensory nerve fiber that can signal the spinal cord, which can activate one or more efferent fibers to reduce the reflex. For example, the one or more efferent fibers can reduce one or more spastic urethral reflexes, which can impede voiding the urinary bladder.

At 42, an electrical waveform (e.g., EW) can be generated (e.g., by waveform generator 12). The electrical waveform can be configured to facilitate reduction of the at least one reflex that affects a bodily function. For example, the electrical waveform can be a patterned waveform. The patterned waveform can include a base frequency. In some instances, the base frequency can be 10 Hz or less. In other instances, the base frequency can be 5 Hz or less. In still other instances, the base frequency can be 1 Hz or less.

A stimulation waveform can be delivered during each duration of the base frequency. In some instances, the stimulation waveform can be delivered during 50% or more of each duration of the base frequency. In other instances, the stimulation waveform can be delivered during 60% or more of each duration of the base frequency. In still other instances, the stimulation waveform can be delivered during 75% or more of the base frequency.

The stimulation waveform can be of a greater frequency than the base frequency. In some instances, the stimulation waveform can have a frequency of more than 10 Hz. In other instances, the stimulation waveform can have a frequency of 15 Hz or more. In still other instances, the stimulation waveform can have a frequency of 20 Hz or more.

At 44, an afferent nerve fiber within a nerve can be stimulated with the electrical waveform (e.g., applied by electrode 14). At 46, a reflex function can be affected.

The afferent nerve fiber can receive a sensory input (e.g., due to the electrical waveform) and transmit a signal (e.g., including one or more action potentials) to a portion of the spinal cord (e.g., the sacral portion of the spinal cord or the lumbar portion of the spinal cord). For example, the sensory input can be received by a dermatome linked to a certain portion of the spinal cord.

In response, the spinal cord can transmit a signal along one or more efferent nerve fibers. The signal (e.g., including one or more action potentials) can be transmitted by the efferent nerve fibers to activate or disable a reflex action that can affect an organ. In some instances, the efferent nerve fibers can be autonomic nerve fibers (e.g., sympathetic nerve fibers and/or parasympathetic nerve fibers).

One example of a reflex can include a urethral reflex (e.g., an external urethral sphincter reflex or an internal urethral sphincter reflex). A method 50 for reducing at least one urethral reflex is shown in FIG. 5. The urethral reflex can impede one or more bodily functions (e.g., voiding the urinary bladder), and the method 50 can enable the one or more bodily functions.

The method 50 can provide a non-destructive, minimally-invasive treatment for spastic urethral reflex contractions. At 52, an electrical waveform (e.g., EW) can be generated (e.g., by waveform generator 12). The electrical waveform can be configured to reduce a urethral reflex that impedes urine flow from a urinary bladder of the subject. For example, the electrical waveform can be a patterned waveform. The patterned electrical waveform that can include a stimulus during at least a portion of the duty cycle. In some instances, the stimulus waveform can be a burst waveform.

At 54, the electrical waveform can be delivered to a nerve that contains at least one afferent nerve fiber. The nerve that includes one or more afferent fibers can be a peripheral nerve, a sacral spinal cord nerve, a sacral root nerve, and/or a lumber spinal cord nerve. The one or more afferent nerve fibers can relay the send a signal induced by the stimulus waveform to the spinal cord. The spinal cord can signal one or more efferent nerve fibers to relax the spastic urethral reflex. When the spastic urethral reflex is relaxed, the urinary bladder can be voided. Accordingly, at 56, the urethral reflex can be reduced to facilitate voiding the urinary bladder.

In some instances, the voiding of the urinary bladder can be activated by a bladder driver. For example, the bladder driver can apply an electrical stimulation to at least one of a sacral root, a bladder efferent nerve, and an afferent-mediated peripheral nerve to activate the urinary bladder for voiding.

V. Examples

The following examples are for the purpose of illustration only and are not intended to limit the scope of the appended claims.

Example 1

This example shows that patterned sacral dermatome stimulation (dependent on stimulation location and stimulus pattern) can provide a non-destructive and non-invasive approach to reduce urethral abnormal reflexes following chronic spinal cord injury (SCI).

Methods

Chronic SCI Animal Model

Four sexually intact adult male cats had extradural sacral electrodes implanted for on-demand bladder drive; a second surgery to transect the spinal cord was carried out after the electrodes had stabilized and animals were deemed behaviorally suitable for chronic SCI maintenance. All procedures were carried out under general anesthesia (ketamine induction, isoflurane maintenance), with prior approval from the Case Western Reserve University IACUC.

Animals first underwent a laminectomy at the L7-S2 level. Tripolar spiral cuff electrodes (Ardiem Medical, Indiana, Pa.) of 1.25 mm diameter were implanted on the extradural sacral roots eliciting the greatest bladder pressures intraoperatively (verified S2 roots post mortem). Electrode leads were tunneled subcutaneously to exit in the inter-scapular region. Animals were fitted with jackets (Lomir Biomedical, Inc., Malone, N.Y.) to protect the lead exit sites.

Animals underwent surgical spinal transection at the T10-T12 vertebral level (after 17 weeks in animals 1-2, 6 weeks in animals 3-4). The dura was exposed through a laminectomy, and the cord cut through a small incision made in the dura with local application of intradural Marcaine 0.25% (Hospira, Inc., Lake Forest, Ill.). Completeness of transection was visually confirmed prior to closure. Following recovery, animals received manual bladder expression 2-3 times daily; reflex defecation circumvented the need for assistive bowel care. A 9 week survival period established a chronic model of abnormal LUT reflexes.

Post mortem dissection was carried out to confirm the spinal root levels, identify any damage to the sacral root or electrode implants, and verify completeness of spinal transection.

Terminal Procedure

Nine weeks post-SCI animals were anesthetized with an IV infusion of alpha-chloralose (75 mg/kg induction, 19 mg/kg supplemental maintenance as needed) (Sigma Alderitch, St. Louis, Mo.). Sub-cutaneous buprenorphine (0.01 mg/kg) was given every 12 hours. Each animal was instrumented with a suprapubic bladder catheter for bladder filling and draining, and measuring bladder pressure. External sphincter and proximal urethral pressures were measured using a 3.5 French catheter (Gaeltec, Isle of Skye, Scotland) mounted with two microtransducer pressure sensors placed into the urethra. The transducer was zeroed to atmospheric pressure prior to use. The gain of the transducer was calculated using a mercury manometer and two-point linear slope. Active urethral pressure profiles (UPP) were conducted to determine the position of the EUS from the external meatus.

Sacral dermatome levels more effectively deliver sensory stimulation to the spinal circuits generating unwanted urethral reflexes. To investigate surface localization effects, the L4 through S4 dermatomes were shaved and prepped with a medical depilatory prior to application of surface electrode patches. Dermatome locations were estimated from published dermatome maps. "Large" surface electrodes (4 cm×4 cm square, Re-Ply Unipatch; Covidien, San Francisco Calif.) were used for gross dermatome localization effects (lumbar vs. sacral dermatomes). "Small" electrodes (2 cm diameter round, Cardinal Health) were used for finer resolution within lumbar and sacral dermatomes. FIG. 6A shows placement of large and small electrodes for spatial differentiation and the general pattern of electrical stimulation.

Data Collection Stimulation Protocol

Bladder contractions were evoked using 5-10 seconds of 20 Hz stimulation on sacral root electrodes. Control trials consisting of bladder drive without any dermatome stimulation were used to consistently evoke EUS reflex activity. Baseline EUS spasticity was defined as the pressure spikes following root stimulation.

Dermatome stimulation consisted of monophasic constant-current pulses of 100 μs (DS7A, Digitimer, Hertfordshire, England). Afferent neurons typically utilize bursts of action potentials with varying burst durations, frequency and inter-burst intervals suggesting that particular stimulation patterns will provide more effective reflex modulation than others. We used cycle time (s), duty cycle (%), and base frequency (Hz) to generate patterned stimuli. Cycle time was fixed at 1 s for all patterns. Duty cycle was varied (25%, 50%, 75%, 100%) for a fixed base frequency (20 Hz). Cycle time and duty cycle are simultaneously described though stimulation ON time and OFF time (FIG. 6B). At 100% duty cycle, representing continuous stimulation, base frequency was varied between 10, 20 and 40 Hz for all animals (except animal 2, which did not respond to 20 Hz). Stimulation amplitude was determined by visible muscle fasciculation; all trials reported were conducted at 90% of fasciculation threshold.

Voiding improvement was investigated by adding (0.75 ON 0.25 OFF, 20 Hz) dermatome stimulation to intermittent sacral root stimulation (2.0 ON 4.0 OFF, 20 Hz) in one animal (#2). Surface stimulation was limited to the "middle" 2 cm round surface electrode (electrode [5], FIG. 6A). Voiding was limited to 4 paired, bladder volume matched control/ dermatome runs. Voiding percentages were calculated for each run; voiding to completion was not attempted.

Data Analysis

In the same animal a 22 gauge stainless steel needle was inserted through the same location and stimulated with (0.75 ON 0.25 OFF, 20 Hz) to test the effect of on urethral reflexes. All data was recorded in a custom designed data-acquisition program (Labview, National Instruments, Austin, Tex.).

Figure 7:
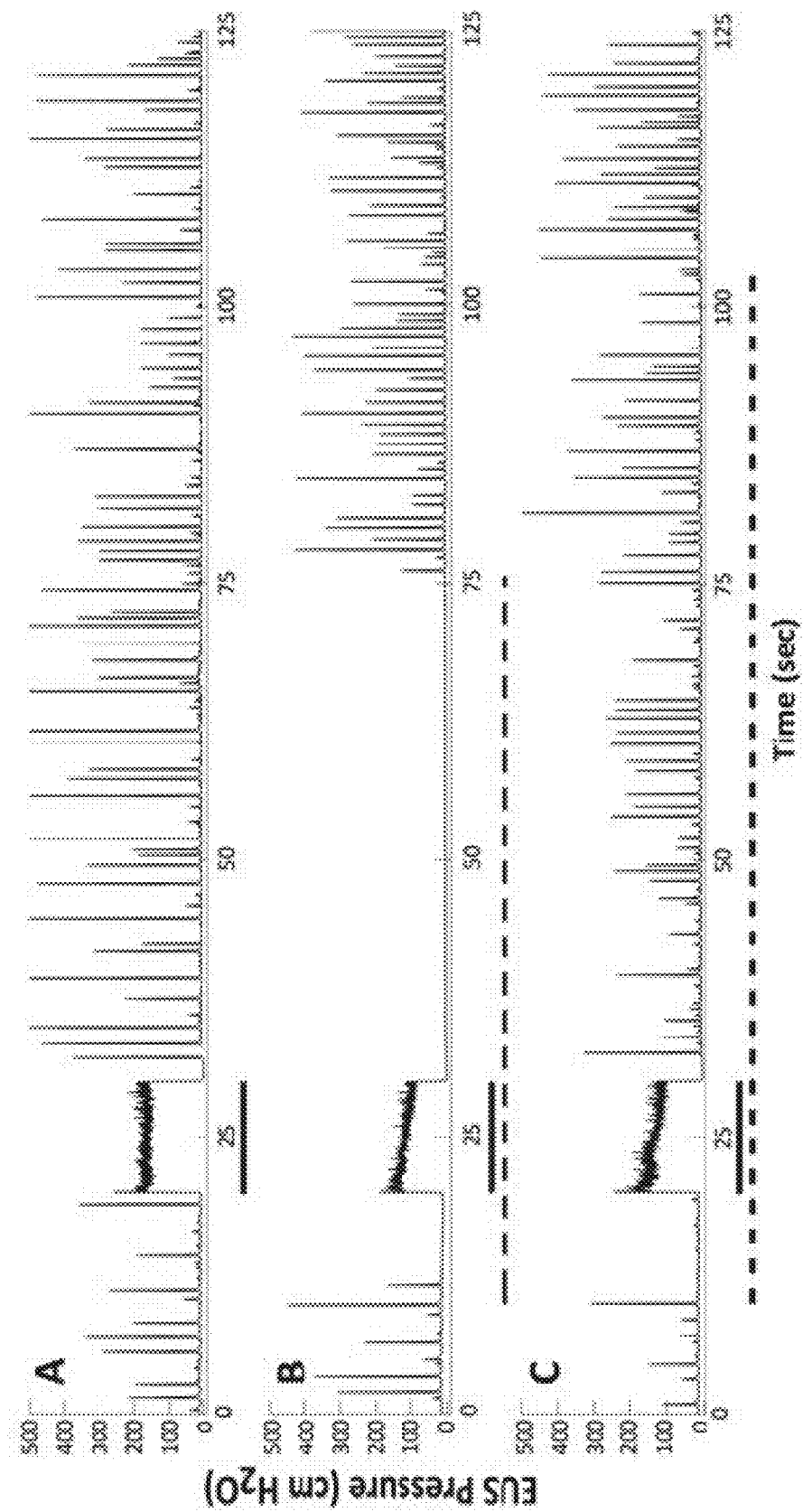
FIG. 7 includes example plots showing the suppression of aberrant urethral reflexes after chronic spinal cord injury (SCI) in felines.

Urethral sphincter spasms were observed as EUS pressure "spikes" in all animals, due to high-fidelity microtransducer recording (FIG. 7). Spike rate and spike amplitude were used as the primary measures of reflex EUS activity. Spikes were defined as pressure increases 1 standard deviation above a 0.5 second moving average, quantified in Matlab (Mathworks, Natick, Mass.). Absolute pressure was used rather than pressure evoked above baseline. Baseline urethral pressure was consistent at ~15 $cmH_2O$. Variables reduced from identified spikes include: Pur=Average urethral spike pressure amplitude ($cmH_2O$) and Rur=Average urethral spike rate (number/sec) calculated over the period of dermatome stimulation (typically 60 seconds), with a corresponding length chosen for comparative control trials.

For each animal one-way ANOVAs were used to analyze the effect of dermatome stimulation on reflex activity when compared to control trials. Additionally ANOVAs were calculated for stimulus patterns at each electrode location, and across locations for each pattern. The Tukey-Kramer method was used to determine which parameter combinations differed significantly; only reductions from baseline which reached ($P<0.05$) significance were labeled "suppression".

Results

Reflex Activity Following Chronic SCI

Prior to SCI, no animals displayed urethral reflex activity under light isoflurane anesthesia. Neither EUS nor bladder activity was evoked when applying dermatome stimulation at sub-fasciculation (4.5-12.5 mA) threshold levels, and current amplitudes high enough to produce urethral pressure changes were inseparable from motion artifact due to hind limb muscle contractions.

The bulbocavernosus reflex reappeared in all animals within 12 hours after SCI and LUT reflexes appeared within 1 week. All animals displayed distention evoked bladder reflexes and the progressive development of spastic urethral sphincter reflexes that were observed under light isoflurane or alpha-chloralose. These EUS reflexes were consistently evoked following sacral root stimulation, however they also occurred spontaneously or with urethral catheter movement. Baseline reflex activity with effective and ineffective patterned surface stimulation are shown in FIG. 7.

Three animals had confirmed complete transection of the spinal cord. Animal 1 had partial voluntary stepping and visceral sensation caudal to transection, suggesting incomplete injury. All animals had at least one working sacral root electrode capable of producing greater than 50 cm $H_2O$ intra-vesicular pressure and greater than 70 cm $H_2O$ urethral sphincter pressure. The right S2 root was damaged in animal 2 during the week after spinal transection.

Effect of Dermatome Stimulation on Urethral Reflex Suppression

Significant, reproducible suppression of urethral reflexes was achieved in 2 of 4 animals when effective stimulus parameters were used (FIG. 7). Reflex reduction was observed within 2 seconds of the start of dermatome stimulation, and was able to be maintained for over 60 seconds. Statistically significant suppression was only achieved for a limited combination of electrode locations and stimulus patterns. Urethral reflexes were reduced by dermatome stimulation at all locations tested in responder animals (1 and 2), but only sacral dermatome locations significantly reduced urethral activity compared to control and were classified as suppression (FIG. 8).

Rur was reduced 92.6% and Pur reduced 61.4% ($P<0.001$) using the large electrode location [S] (animal 1, 20 Hz continuous). Sacral [S] stimulation with (0.75 ON 0.25 OFF, 20 Hz) produced comparable suppression to 20 Hz continuous stimulation (FIG. 9); 20 Hz continuous data are presented as lumbar stimulation [L] was not attempted using (0.75 ON 0.25 OFF, 20 Hz).

Finer resolution of the sacral skin beneath [S] using smaller electrodes [1-5] (animal 2) demonstrated finer spatial resolution within the sacral dermatomes. Locations [4] and [5] both significantly suppressed urethral reflexes. Location [5] reduced Pur 80.8% and Rur 86.1% ($P<0.001$) using (0.75 ON 0.25 OFF, 20 Hz). Suppression was not achieved at electrodes [1-4] for any other patterns tested (data not shown).

Figure 8:
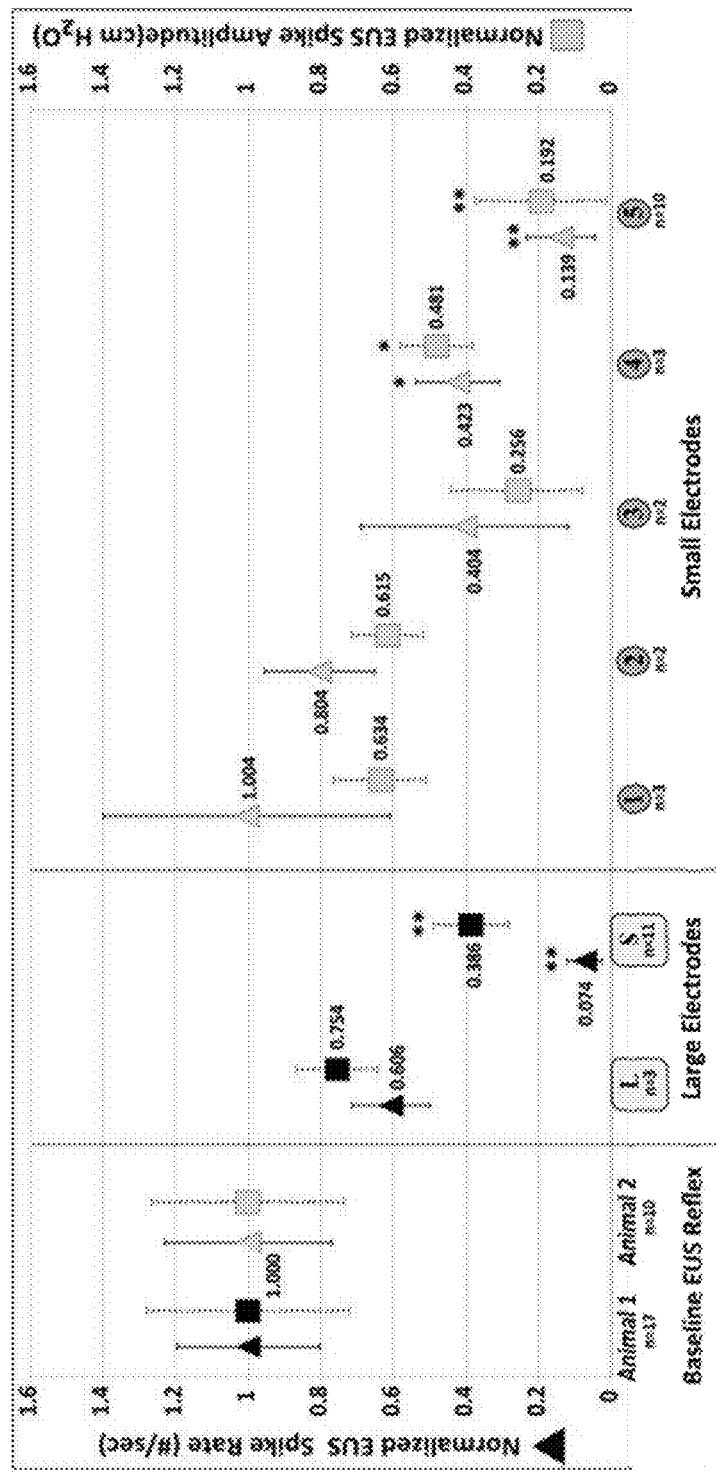
FIG. 8 shows an example diagram illustrating the spatial selectivity of stimulus location for reducing aberrant urethral reflexes in felines.
Figure 9:
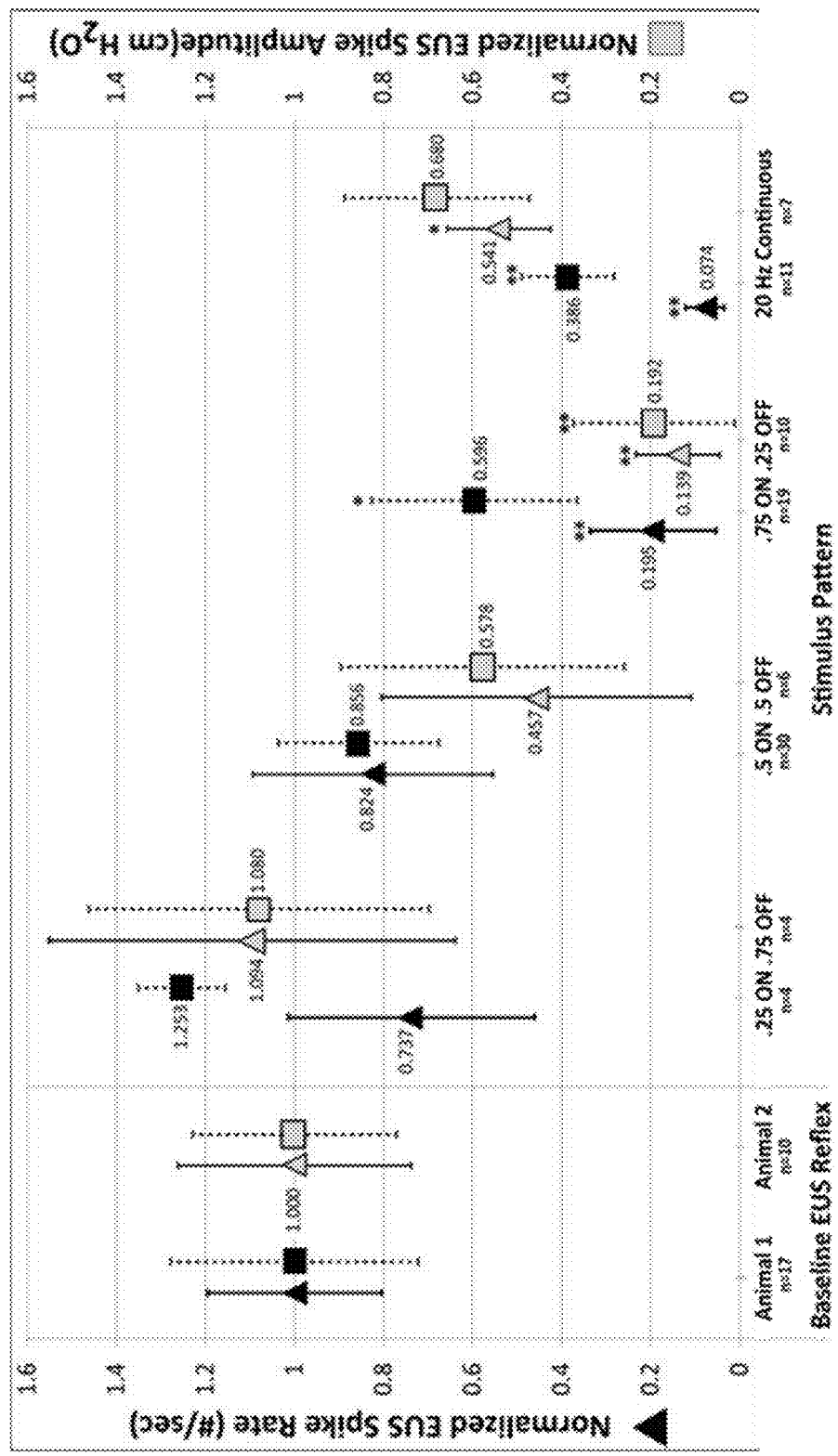
FIG. 9 shows an example diagram illustrating that the choice of stimulus parameters affects the reduction of aberrant urethral reflexes in felines.

Data shown in FIGS. 8 and 9 were normalized to the control for each animal. The Pur and Rur, control values for all animals are shown in Table 1.

TABLE 1

| ANIMAL | CONTROL | | | DERMATOME | | |
|---|---|---|---|---|---|---|
| | Trials (n) | Rur (spikes/sec) | Pur (cm H2O) | Trials (n) | Rur (spikes/sec) | Pur (cm H2O) |
| 1 | 20 | 0.438 ± 0.171 | 167.8 ± 93.4 | ** | | |
| 2 | 24 | 0.088 ± 0.041 | 355.5 ± 186.4 | | | |
| 3 | 21 | 0.188 ± 0.012 | 167.2 ± 100.8 | 83 | 0.199 ± 0.099 | 157.3 ± 121.1 |
| 4 | 24 | 0.054 ± 0.031 | 140.3 ± 59.0 | 49 | 0.078 ± 0.032 | 205.2 ± 79.3 |
| Pooled | 89 | 0.181 ± 0.061 | 210.8 ± 110.9 | 132 | 0.154 ± 0.100 | 175.1 ± 109.7 |

Listing the individual and pooled baseline urethral reflex measures (Pur, Rur, control) for all four animals.

The pooled values for all dermatome stimulation trials are also shown for animals 3 and 4, where no differences were observed between surface stimulation and control for any stimulus locations or patterns tested. Only (0.75 ON 0.25 OFF, 20 Hz) patterned stimulation produced suppression in both responder animals, when applied at effective locations. Increasing duty cycle from 25% to 75% led to progressive reductions in spike rate Rur and amplitude Pur, however only 75% produced suppression compared to control and were classified as suppression. FIG. 9 shows patterned stimuli tested at electrode locations [S] (animal 1) and [5] (animal 2). Data are normalized to the control for each animal.

Continuous (20 Hz) stimulation produced suppression in animal 1, but not animal 2. In animal 1, 10 Hz continuous reduced Rur by 82.4% (P<0.001) and Pur by 28.2%, (P=0.053) and 40 Hz continuous reduced Pur 38.1% (P=0.289) and Rur 60.1% (P=0.084).

Bladder emptying was improved from 30.3%±3.8% (8.95±2.2mL) without dermatome stimulation to 41.93%±6.6% (12.43±2.9 mL) with stimulation (P<0.05) in single bladder drive-limited stimulus runs. When normalized to control voided volumes, this represents a 38.3%±21.7% increase with the addition of effective surface stimulation. Bladder volume for all trials was 29.3 mL±3.5 mL.

Subcutaneous stimulation reduced Rur (P<0.01) and Pur (P<0.001) when compared with control trials. Subcutaneous stimulation was not significantly different from surface stimulation using the same (0.75 ON 0.25 OFF, 20 Hz) pattern (Rur (P=0.362), Pur (P=0.771)). In 7 subcutaneous trials, (Rur=0.0208±0.019/sec; Pur=83.95 ±88.21 cm $H_2O$).

Example 2

This example shows that patterned sacral afferent stimulation can produce effective voiding in animals with chronic SCI. However, stimulation parameters and locations described below that are used to produce effective voiding in animals may be need to be changed to produce effective voiding in humans.

Methods
Chronic SCI Animal Model

Four sexually intact adult male cats had extradural sacral electrodes implanted to generate on-demand bladder pressure. Spinal transection was carried out after electrode performance was verified and animals were deemed behaviorally suitable for chronic SCI (6 weeks post-implant). Animals underwent a terminal experiment under alpha-chloralose anesthesia 9 weeks post SCI; a suprapubic bladder catheter was placed to measure bladder pressures during the terminal experiment. All surgical procedures were carried out under general anesthesia (ketamine induction, isoflurane maintenance), with prior approval from the Case Western Reserve University IACUC.

Urethral Reflex Suppression

Animals were tested every two weeks under light propofol IV anesthesia (PropoFlo 28, Abbot Animal Health; 1 mg/kg induction, 0.4-0.6 mL/min maintenance, 10 mg/mL) beginning one week post spinal transection. Urethral reflexes were continuously monitored using a high-fidelity 3.5 French microtransducer catheter (Gaeltec, Isle of Skye, Scotland). Stimulation parameters and paradigms were consistent with methods reported previously. Sacral (L7-S3) dermatomes were shaved and prepped with a medical depilatory prior to application of surface electrode patches. Effective dermatome locations were found by probing a 2 cm round Ag/AgCl disk electrode (Cardinal Health, US) across the sacral dermatomes thinly coated with electrolytic gel (Spectra 360, Parker Laboratories). Stimulation patterns previously found to produce effective urethral reflex suppression were delivered to the sacral dermatomes, typically (0.75 sec ON, 0.25 sec OFF, 20 Hz) and 20 Hz continuous stimulation. Stimulation amplitude was set to 90% of the visible muscle fasciculation threshold. Skin locations that visibly reduced EUS spike activity were marked and surface patch electrodes (2 cm diameter round, Cardinal Health) were placed over the effective location. The target electrode was bounded by additional electrodes in the rostral/caudal and medial/lateral directions to verify spatial selectivity.

Voiding Protocol: Voiding Under Anesthesia

Bladder contractions were produced using sacral root stimulation (20 Hz, 2 s ON, 4 s OFF) to obtain consistent, reproducible bladder pressures. Intermittent stimulation is utilized in existing human neuroprostheses because sacral stimulation activates both the bladder and sphincter; voiding occurs during the stimulation OFF periods. However urethral reflexes after SCI prevent voiding and sacral dorsal rhizotomy is required to achieve clinically acceptable voiding in humans.

Figure 10:
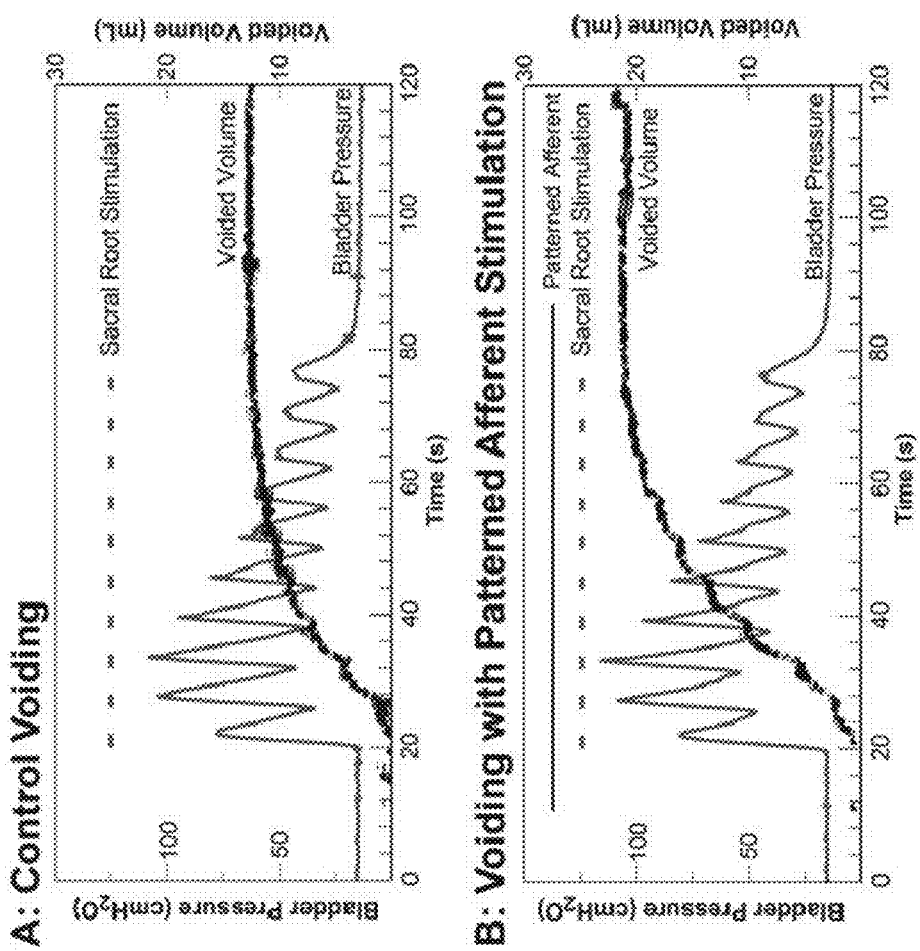
FIG. 10 shows sample voiding traces in felines with an without afferent stimulation.

Bladder voiding was evaluated during bladder activation with and without PSAS. Voiding was initially tested under propofol anesthesia before being tested in awake-behaving animals. During anesthetized tests bladder and sphincter pressures were evaluated under isovolumetric conditions prior to voiding. FIG. 10 illustrates the typical bladder pressure and voiding pattern produced by the control and afferent voiding paradigms.

Awake Voiding

Unanesthetized tolerance for sacral root stimulation was verified before awake voiding was conducted. Intermittent root stimulation was delivered for 60 to 90 seconds in each run. Runs were repeated 5 (range 3-7) times with 3 minutes of rest in between to allow recovery of any detrusor muscle fatigue. Voided volumes were measured in mL for each stimulation run. Residual volumes were calculated for anesthetized voids via intraurethral catheterization. Residual volumes for awake voiding trials were found via manual expression following electric voiding, or by bladder palpation during the bladder maintenance phase. Palpation estimates were calibrated during acute testing sessions with known bladder volumes.

Daily Maintenance Voiding

Electric voiding was considered successful if the total percentage emptied was greater than or equal to the average manually expressed percentage for each animal. Manual expression is the clinical standard of care for maintaining chronic SCI cats. After demonstrating successful awake voiding with PSAS, an animal was transitioned to the electric maintenance phase replacing twice daily manual expression with electric voiding as the primary method of bladder emptying. Electric maintenance was suspended temporarily when animals were transferred out of the facility on weekends, holidays, and for bi-weekly anesthetized testing sessions. Animals were voided twice (range 1-4) daily with electrical stimulation separated by 8-12 hours. Voiding was repeated at shorter intervals in cases of high urine output or large estimated residuals.

Subcutaneous Stimulation and Cutaneous Anesthesia

During the terminal test in animal 4, afferent stimulation was delivered subcutaneously through a 22 gauge hypodermic needle inserted parallel to the skin surface immediately beneath the effective surface location (left side). Voiding with needle stimulation was conducted in 2 sets of control and afferent runs following successful reflex suppression.

In the same experiment lidocaine gel (Topicaine 4%, ESBA Laboratories) was applied topically to the effective dermatome location (right side) to produce local anesthesia of cutaneous afferents. The gel was removed after 10 minutes, and surface stimulation reapplied to the effective area. Standard reflex measures were compared for (0.75 ON, 0.25 OFF 20 Hz) stimulation afferent suppression before and after lidocaine anesthesia.

Data Analysis

Reflex activity was quantified by pressure spike rate and spike height. Each metric was compared between control conditions (without PSAS) and with PSAS and analyzed as described previously. Voiding efficiency was compared between conditions (intermittent root voiding with and without PSAS, and manual expression) using bladder volume and total percentage voided. For each animal one-way ANOVA was used to analyze the effect of dermatome stimulation on bladder voiding when compared to control stimulation and hand expression. Tests were conducted separately for volumes and percentages. The Tukey-Kramer method was used to identify post-hoc significance ($\alpha=0.05$).

Results

Suppression of EUS Reflex Activity

All animals demonstrated active urethral reflexes within 1 week after SCI, and reflex bladder contractions by 3 weeks post SCI. Urethral reflex suppression was achieved in two of four animals (animals 1, 4) using PSAS patterns previously identified (0.75 ON, 0.25 OFF 20 Hz) and (20 Hz continuous). Suppression was first achieved during propofol-anesthetized tests 35 days ($3^{rd}$ test, animal 1) and 21 days ($2^{nd}$ test, animal 4) after SCI. Unilateral sacral dermatome stimulation reduced reflex spike rate from ($0.129\pm0.014$ to $0.016\pm0.012$ spikes/second, $p<0.001$) and spike amplitude from ($141.8\pm14.8$ to $80.2\pm15.4$ cmH$_2$O, $p<0.001$). Surface suppression was achieved on only the left side dermatomes in animal 1 and on both sides in animal 4. PSAS amplitudes for successful suppression leading to voiding were $5.6\pm1.7$ mA.

Two animals (animals 2, 3) did not demonstrate a significant reduction in urethral reflex activity in response to any PSAS parameters tested. These animals therefore did not advance to the voiding stages of the protocol. All animals had complete spinal transections, confirmed post mortem. Urethral reflex activity features were consistent for all types of anesthesia used (propofol IV, alpha-chloralose) across all animals. The ability to demonstrate suppression of reflexes and voiding improvement was independent of anesthetic, including unanesthetized conditions.

Voiding Under Anesthesia

Figure 11:
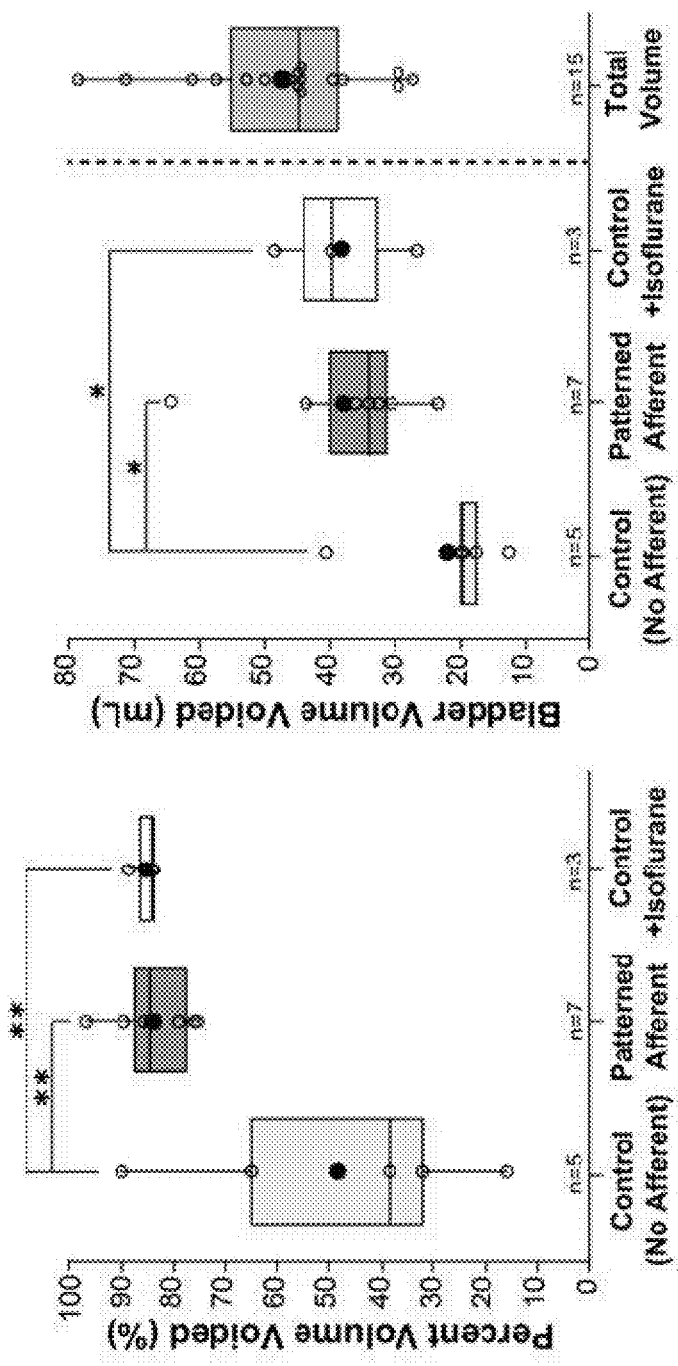
FIG. 11 shows a plot of feline voiding under light anesthesia with afferent stimulation.

Bladder voiding with PSAS was superior to sacral root stimulation alone under light propofol anesthesia in both animals (FIG. 11). Data are pooled across animals. Sacral root stimulation alone (n=5) produced $48.3\pm11.75\%$ bladder emptying, with an average voided volume of $22.0\pm10.76$ mL. Reducing urethral pressures with PSAS (n=7) improved voiding to $83.9\pm6.2\%$ ($p<0.01$), with an average voided volume of $37.8\pm7.0$ mL ($p<0.05$). The addition of deep isoflurane anesthesia completely eliminated urethral reflexes and provided a measure of the maximum voiding efficiency possible. Control sacral root stimulation under isoflurane (n=3) produced $85.3\pm3.0\%$, $38.2\pm9.2$ mL voiding, not significantly improving percentage ($p=0.629$) or volume ($p=0.949$) from afferent voiding.

Isovolumetric pressure recordings confirmed that surface stimulation did not impact bladder pressures during sacral root stimulation driven contractions. Surface stimulation also did not affect the magnitude or duration of distension-evoked reflex bladder pressures. Therefore increased bladder pressure was not the cause of improved voiding.

Awake and Daily Maintenance Voiding

Following voiding improvement with PSAS under anesthesia, animals 1 and 4 began awake testing 50 and 22 days post SCI, respectively. Forty-four total sessions of afferent voiding and eighteen control sessions were completed across both animals. Eight afferent sessions and two control sessions were excluded from awake statistical analysis due to electrode connectivity issues in one or more stimulation runs.

Figure 12:
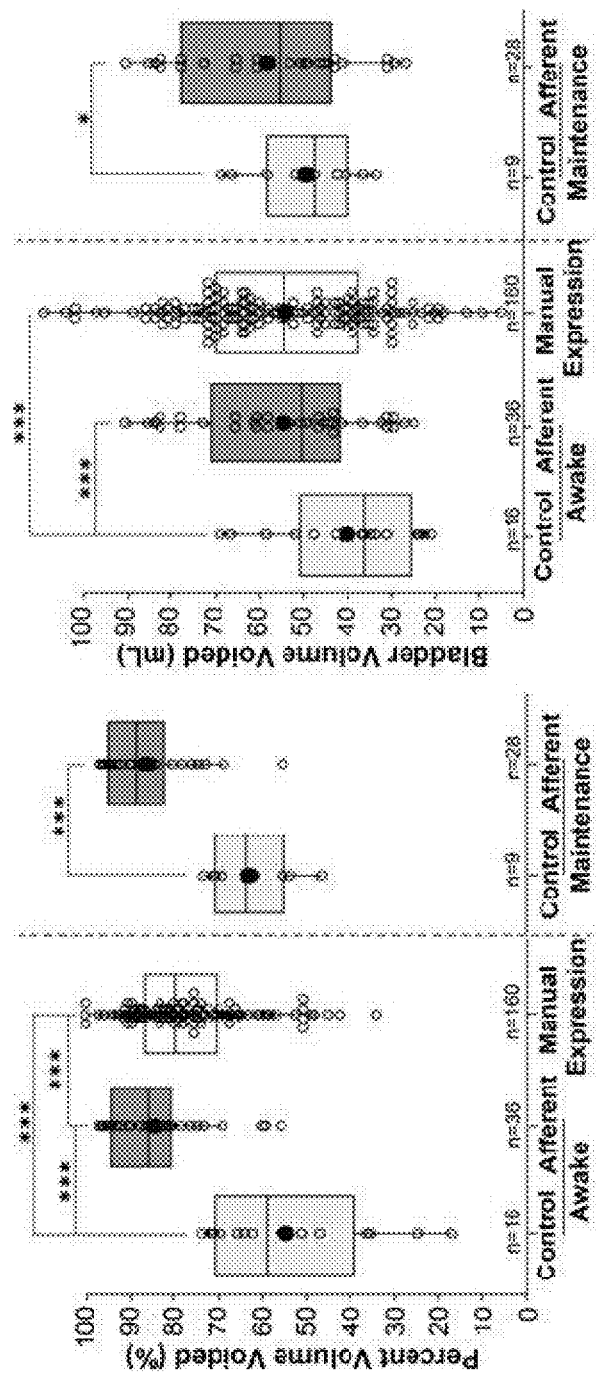
FIG. 12 shows a plot of awake feline voiding with afferent stimulation compared to manual expression.

Bladder voiding with PSAS ($84.6\pm10.9\%$) was superior to voiding without PSAS ($54.3\pm17.9\%$) under awake-behaving conditions in both animals (FIG. 12). Manual expression voided 76% (n=112) of bladder volume in animal 1 and 80% (n=48) in animal 4. Twenty-nine of thirty-six voids with PSAS were equivalent to or greater than manual expression. Zero of sixteen control voids were greater than manual expression.

Additional awake stimulation runs produced diminishing returns toward total voided volume. The percentage of total starting volume contributed by individual stimulation runs were [13.4%; 12.3%; 9.1%; 7.9%; 7.3%] for control and [32.2%; 21.7%; 22.8%; 3.6%; 2.1%] when PSAS was added. All awake voids used at least 5 stimulation runs to maximize bladder emptying.

Figure 13:
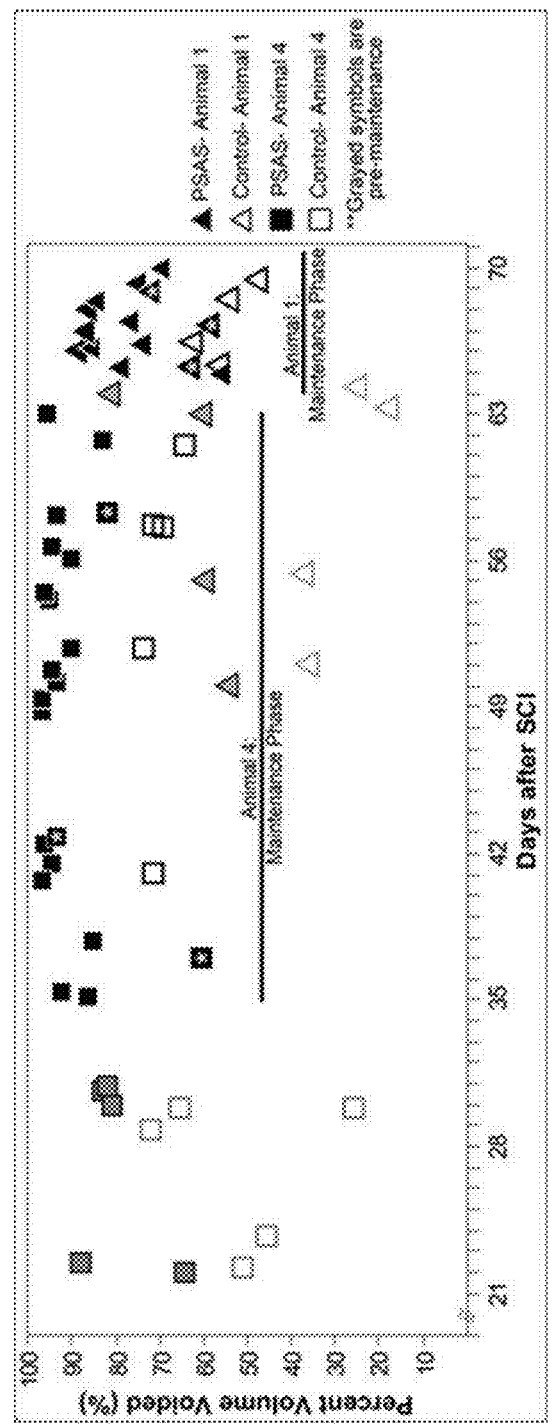
FIG. 13 shows a plot of feline daily maintenance voiding with afferent stimulation over time.

Both animals transitioned to the maintenance voiding phase (animal 1: 65 days post-SCI; animal 4: 36 days post-SCI) where electric voiding was used twice daily to replace manual expression (FIG. 13). Six maintenance voids shown in FIG. 13 had stimulation problems in the first 5 runs and were therefore excluded from statistical analysis (not shown in FIG. 12). Twenty-five of twenty-eight afferent voids were greater than manual expression percentage while zero of nine control maintenance voids were. Both animals maintained low residual volumes without habituation or appreciable loss of reflex suppression during daily use. Stimulation ($6.6\pm1.9$ minutes/episode, range 5.0-10.5) was delivered 1.9±0.7 (range 1-4) times/day. At most, stimulation of 30 minutes/day was sufficient to replace other bladder maintenance methods.

Subcutaneous Stimulation and Cutaneous Anesthesia

Subcutaneous afferent stimulation (20.9 mA) reduced EUS pressures consistent with surface stimulation (0.071±0.129 spikes/second; 56.8±51.6 $cmH_2O$). Voiding using subcutaneous PSAS (91.9±1.7%) was comparable to voiding using surface afferent stimulation.

Lidocaine gel eliminated surface reflex suppression. Surface stimulation of (0.75 ON 0.25 OFF, 20 Hz) on the right S1-S2 dermatome suppressed reflex spikes prior to gel application. Repeating afferent stimulation after cutaneous anesthesia failed to produce any reduction in either spike rate or spike amplitude.

From the above description, those skilled in the art will perceive improvements, changes and modifications. Such improvements, changes and modifications are within the skill of one in the art and are intended to be covered by the appended claims.

What is claimed is:

1. A method comprising the steps of:
generating, by a waveform generator, an electrical waveform comprising cycles of an on time that comprises a patterned electrical waveform, comprising a base waveform and a burst waveform occupying 75% of the base waveform, and an off time; and
delivering, by an electrode coupled to the waveform generator, the electrical waveform to a dermatome of a nerve comprising afferent nerve fibers of the subject to stimulate the afferent nerve fibers to suppress a urethral reflex that impedes urine flow and affects a bodily function.

2. The method of claim 1, wherein the electrode is a surface electrode or a subcutaneous electrode.

3. The method of claim 1, wherein the bodily function comprises voiding the urinary bladder.

4. The method of claim 3, further comprising stimulating, by a bladder driver, a second nerve to activate the urinary bladder to facilitate the voiding when the urethral reflexes are reduced.

5. The method of claim of claim 1, wherein the nerve is at least one of a peripheral nerve, a sacral spinal cord nerve, a sacral root nerve, a thoracic spinal nerve, and a lumbar spinal cord nerve.

6. The method of claim 4, further comprising applying, by the bladder driver, electrical stimulation to at least one of a sacral root, a bladder efferent nerve, and an afferent-mediated peripheral nerve to activate the urinary bladder for voiding.

7. The method of claim 1, wherein the nerve is a sacral afferent nerve.

* * * * *